(12) United States Patent
Li et al.

(10) Patent No.: US 9,398,797 B2
(45) Date of Patent: Jul. 26, 2016

(54) NAIL GAUGE MEASURING NAIL SHAPE AND NAIL ARC LENGTH

(71) Applicants:Yong Li, LaSalle, CA (US); Kefei Wang, Beijing (CN); Yinhong Zhao, Beijing (CN)

(72) Inventors: Yong Li, LaSalle, CA (US); Kefei Wang, Beijing (CN); Yinhong Zhao, Beijing (CN)

( * ) Notice: Subject to any disclaimer, the term of this patent is extended or adjusted under 35 U.S.C. 154(b) by 512 days.

(21) Appl. No.: 13/731,179

(22) Filed: Dec. 31, 2012

(65) Prior Publication Data

US 2014/0182151 A1     Jul. 3, 2014

(51) Int. Cl.
*A45D 29/00*  (2006.01)
*A61B 5/00*  (2006.01)
*A61B 5/107*  (2006.01)
*G01B 3/56*  (2006.01)
*G01B 3/34*  (2006.01)

(52) U.S. Cl.
CPC .............. *A45D 29/00* (2013.01); *A61B 5/107* (2013.01); *A61B 5/449* (2013.01); *G01B 3/34* (2013.01); *G01B 3/56* (2013.01)

(58) Field of Classification Search
CPC ....... A45D 29/05; A45D 29/00; A61B 5/107; G01B 3/34; G01B 3/56
USPC ............ 33/511–512, 501.05, 501.08, 501.09, 33/501.45, 514.1, 514.2, 483–487, 33/492–494, 679.1; D28/56, 99; 132/73.5, 132/75.6, 76.4, 200
See application file for complete search history.

(56) References Cited

U.S. PATENT DOCUMENTS

| | | | | |
|---|---|---|---|---|
| D22,531 S | * | 6/1893 | Ford | D10/64 |
| 1,512,364 A | * | 10/1924 | Rose | 132/230 |
| 1,881,651 A | * | 10/1932 | Judge | 33/562 |
| 2,247,567 A | * | 7/1941 | Wendell | 132/75.6 |
| 3,209,463 A | * | 10/1965 | Schorr | 33/199 R |
| 3,722,104 A | * | 3/1973 | Enzetti | 33/512 |
| 4,140,139 A | * | 2/1979 | Aylott | 132/73 |
| 4,361,160 A | * | 11/1982 | Bryce | 132/73 |
| D293,839 S | * | 1/1988 | Wienslaw | D28/99 |
| D299,878 S | * | 2/1989 | Wienslaw | D28/99 |
| D309,196 S | * | 7/1990 | LaJoie | D28/56 |
| D319,404 S | * | 8/1991 | Jackson, Sr. | D10/64 |
| 5,070,892 A | * | 12/1991 | Trematerra | 132/73 |
| D386,823 S | * | 11/1997 | Carroll et al. | D28/56 |
| 5,901,714 A | * | 5/1999 | Benkart | 132/285 |
| 5,918,375 A | * | 7/1999 | Rossi, III | 33/485 |
| 5,988,178 A | * | 11/1999 | Bair | 132/73 |
| 6,012,461 A | * | 1/2000 | McKew | 132/73 |
| D445,348 S | * | 7/2001 | Trainor | D10/64 |
| 7,123,983 B2 | * | 10/2006 | Yogo et al. | 700/182 |
| D637,500 S | * | 5/2011 | Corbin | D10/64 |
| 2003/0019120 A1 | * | 1/2003 | Davenport | 33/512 |
| 2009/0092310 A1 | | 4/2009 | Gifford et al. | |
| 2012/0132221 A1 | | 5/2012 | Kergosien | |
| 2014/0183769 A1 | * | 7/2014 | Li et al. | 264/40.1 |

* cited by examiner

*Primary Examiner* — R. A. Smith
*Assistant Examiner* — Tania Courson
(74) *Attorney, Agent, or Firm* — Howard & Howard Attorneys PLLC

(57) ABSTRACT

A nail gauge tool is provided for quickly and accurately measuring nail shape and nail size. The nail gauge offers several arch-shaped openings for matching to and measuring a natural nail. As the measurement result, the nail arch shape information and nail arc length information along the natural nail's width direction are obtained for manufacturing custom-fit artificial nails. The nail gauge tool is advantageously small and suitable for use inside a nail salon.

7 Claims, 3 Drawing Sheets

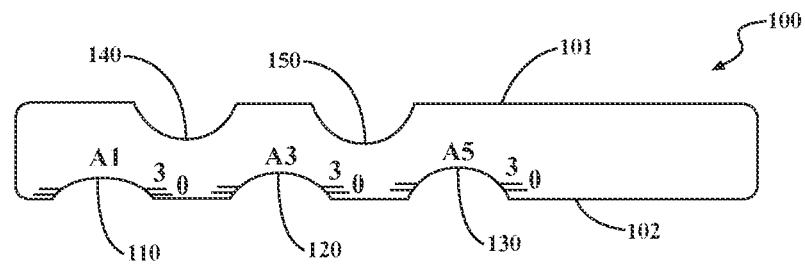
FIG. 1
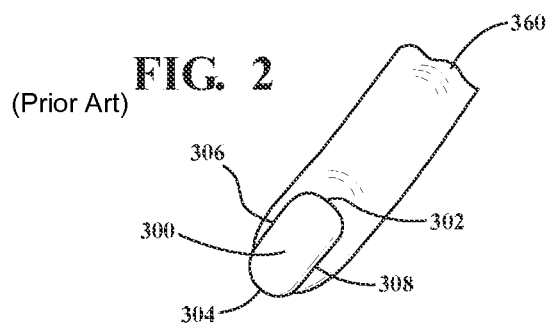
(Prior Art) FIG. 2
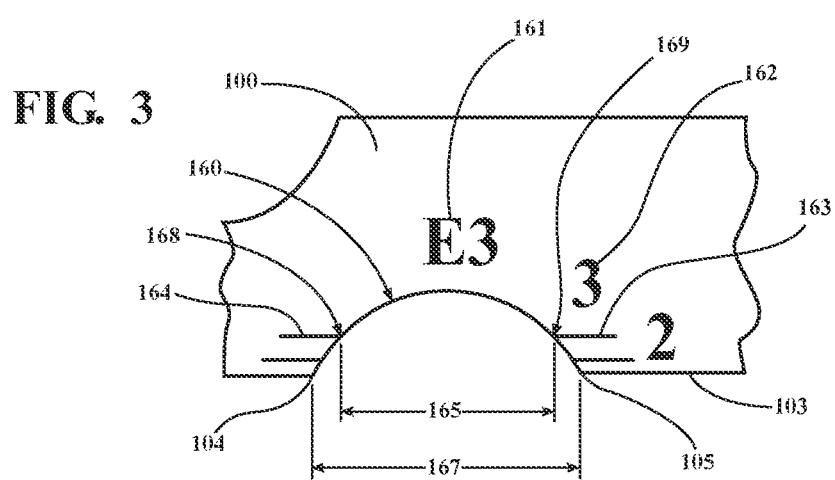
FIG. 3

NAIL GAUGE MEASURING NAIL SHAPE AND NAIL ARC LENGTH

FIELD OF THE INVENTION

The present invention relates to the field of manufacturing custom-fit three-dimensional ("3D") artificial nails including fingernails and toenails. The invention more specifically relates to a novel nail gauge tool which can measure nail arch shape and nail arc length.

BACKGROUND OF THE INVENTION

Artificial fingernails and toenails (collectively "nails") are applied on top of natural nails as a desirable fashion accessory. There are several ways to create artificial nails, such as acrylic nails, gel nails, nail wraps, and full-coverage pre-made nail tips. In order to maximize appearance, durability and comfort on the wearer's finger or toes, it is desirable that the artificial nails fit a user's natural nails properly both in size and shape (where shape includes the contour of the nail). However, the size and shape of a natural nail, for example a fingernail, varies from one finger to another and from one person to another person. Properly fitting an artificial nail onto each of a wide variation of shapes and sizes of natural nails is challenging.

Customized methods, such as acrylic nails and gel nails, are made directly onto each natural finger to fit the exact contour and dimensions of natural nails. However, these custom-made methods are very labor intensive and time consuming. Acrylic nails and gel nails are not re-usable. Once applied, acrylic nails and gel nails will stay on a natural finger all the time until the user takes action to dissolve them into acetone. In addition, the growth of a natural nail will create a gap between its cuticle and the artificial nail, which needs to be filled regularly. Use of acrylic nails and gel nails also creates some health concerns since these materials and their methods of application expose both the user and nail technician to chemical fumes and filing debris. In addition, having a natural nail covered by an artificial nail constantly for a long period of time can seriously damage the nail bed and hamper natural nail growth.

As an alternative to the above-described customized methods, pre-made full-cover nail tips can be applied and removed easily. However, mass-produced nail tips are not customized to a certain user. They are typically made in limited sizes, shapes and styles, and sold in packages containing ten or more nail tips in different sizes, shapes and styles. It is impractical to use an injection molding method to mass-produce artificial nails with massive variations in widths, arch heights, and curvatures that can accommodate all natural nails. As a result, manufactures typically produce a set of pre-formed artificial nails, which has varying widths with a set degree of curvatures. However, a user frequently finds that the available pre-made and pre-packaged nail tips are inadequate to provide the user a proper-fitting artificial nail for each finger. As a consequence, the artificial nails are usually forced into conformity with the contours of the natural nail and then glued onto the natural nail by using an adhesive. However, forcing the artificial nails to conform to the contours of the natural nails means the artificial nails are always seeking to return to their original shape. As a result, not-properly-fitted artificial nails lift up and peel off easily and quickly. In addition, improperly fitted artificial nails leave a space between themselves and the natural nails, which creates an area where bacteria and fungus can potentially develop.

In view of the foregoing, it would be desirable to have a system and process to create custom-fit artificial nails quickly and easily without compromising the health of both the user and the nail technician. U.S. Pat. No. 7,123,983 titled "System and Process for Creating Custom Fit Artificial Fingernails Using a Non-Contact Optical Measuring Device" to Yogo et al. uses an optical 3D measuring device to digitize the topographical configuration of a natural nail surface and then an artificial nail is digitally designed. This system uses a computer numerical controlled ("CNC") machine to mill out each artificial nail. This direct CNC machining method can ensure proper-fit but is still very time consuming, costly and requires considerable work to turn a machined piece into the final artificial nail. In addition, it is also not desirable to perform the CNC machining in a nail salon environment and usually an off-site machining center is needed. As a result, a user cannot have the artificial nails done on-site right after the measuring and has to wait for shipping of the custom-fit artificial nails. Therefore, there is a need for a way to create custom-fit artificial fingernails without these limitations and potential problems.

In view of the foregoing, and as part of an improved way of manufacturing custom-fit artificial fingernails it would be desirable to have a device or tool to measure a natural nail's topographical information, such as nail arch shape and nail arc length, and provide improved accuracy for using this information to create custom-fit artificial nails.

SUMMARY OF THE INVENTION

The present invention provides a nail gauge tool to easily and effectively measure a natural nail to obtain the nail shape and nail arc length information along the nail width direction. In a preferred embodiment of the present invention, the nail gauge has a plurality of arch-shaped openings, and each opening has a pre-defined shape assigned with a specific code. On the both sides of the opening, there are markings, such as lines, to correspond to certain nail arc lengths and nail sizes. In use, the nail gauge is placed directly on the natural nail such that one of the arch-shaped openings in the nail gauge is matched to the nail shape. Markings on the matching opening are then matched to the nail edge thus providing a measurement of the nail shape and nail arc length. This information is then recorded and can be used for selection of a matching or near-matching artificial nail. In addition, the nail gauge tool and resulting measurement information is useable for deciding on an appropriate artificial nail blank that will be further modified in order to create a custom-fit artificial nail.

Other objects and features of the present invention will become apparent when viewed in light of the detailed description of the preferred embodiments when taken in conjunction with the attached drawings and appended claims. However, it is to be understood that the drawings are not necessarily drawn to scale and are designed solely for purposes of illustration and not as a definition of the limits of the invention.

BRIEF DESCRIPTION OF THE DRAWINGS

The novel features of the present invention, as well as the preferred embodiments of the present invention will be best understood from the accompanying drawings, taken in conjunction with the accompanying description, in which similar reference characters refer to similar parts, wherein:

FIG. 1 is a front view of a nail gauge according to a preferred embodiment of the present invention;

FIG. 2 (Prior Art) is a perspective view of a natural nail;

FIG. 3 is a close-up view of one of the arch-shaped openings of the nail gauge;

DETAILED DESCRIPTION OF THE INVENTION

Figure 4:
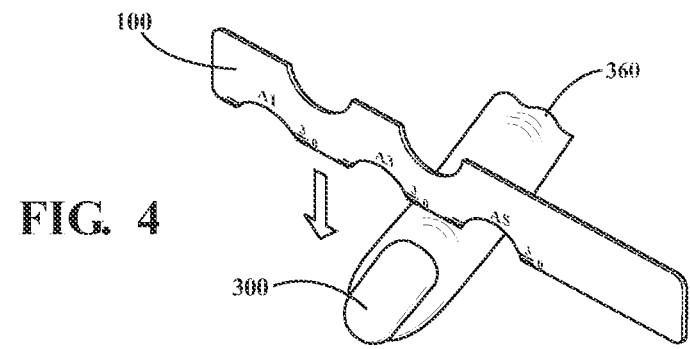
FIG. 4 is a perspective view of using the nail gauge to measure a fingernail.

The following description of the preferred embodiments is merely exemplary in nature and it in no way intended to limit the invention, its application or uses. Those skilled in the art will recognize various alternative embodiments.

Referring to FIGS. 1-3, a nail gauge 100 of the present invention has a generally rectangular shape with a top edge 101 and bottom edge 102. The nail gauge 100 includes a first 110, second 120 and third 130 arch-shaped openings along bottom edge 102, which are designated as "A1", "A3", and "A5", respectively. A first 140 and second top-side 150 arch-shaped openings are located along the top edge 101, which are designated as "A7" and "A9" (on the back of the nail gauge, not seen in FIG. 1) respectively. An arch-shaped opening is formed by a curved edge 160, which intersects with nail gauge edge 103 at a first point 104 and a second point 105. The curved edge 160 has a specific curved shape, which is unique for the nail gauge and is designated by a code "E3". The curved edge 160 can be a circular shape or it can be any free-form curve but generally has a concave form. The straight-line distance 167 between the first point 104 and second point 105 is the width identified with the E3 code name. The arc length of the curved edge 160 is the distance travelled along the curved edge 160 between any two points on the curved edge. A numerical number or code can be assigned to represent different arc lengths. For example, an arc length of 20 millimeter can be called arc length "0" and an arc length of 18 millimeter can be called arch length "1", etc. Different arc lengths are marked next to the curved edge 160 by a line segment. For example, first line segment 163 and second line segment 164 are parallel to the nail gauge edge 103 and intersect with the curved edge 160 at a first marker 168 and a second marker 169. The arc length identifier 162, between the first marker 168 and second marker 169 is designated as numerical number "3" in close proximity to the first line segment 163. An arch-shaped opening can have multiple arc length markers. As shown (FIG. 3), the arch-shaped opening E3 has two arc length markers "2" and "3".

A natural nail 300 is a three-dimensional body which has a proximate edge 302 called a cuticle, a distal edge 304 sometimes extended beyond the fingertip, a first side edge 306 and a second side edge 308. The straight-line distance between the first side edge 306 and second side edge 308 is called the "nail width" and the straight-line distance from the proximate edge 302 to the distal edge 304 is called the "nail length." A natural nail has a curved form with a curvature between the first side edge 306 and second side edge 308 being called the "arch shape." The arc length along nail width direction is defined as the distance travelled from the first side edge 306 along nail curved surface to the second side edge 308. A natural nail also has a relatively flatter, but in most cases, curved form from the cuticle to the distal edge. The arch shape along the nail width direction varies a lot from finger to finger and from person to person. On the other hand, the curved form from the cuticle to the distal edge does not tend to vary as significantly. In order to properly apply an artificial nail onto a natural nail and leave no, or, minimum gap in-between, the arch shape and arc length of both the artificial nail and the natural nail should substantially be the same. The nail gauge 100 provides an easy to use tool for facilitating a match in the shape and size of an artificial nail and the natural nail 300.

Figure 5:
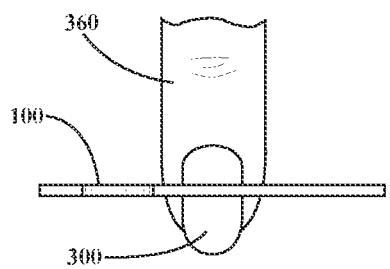
FIG. 5 is a top view of using the nail gauge to measure a fingernail.
Figure 6:
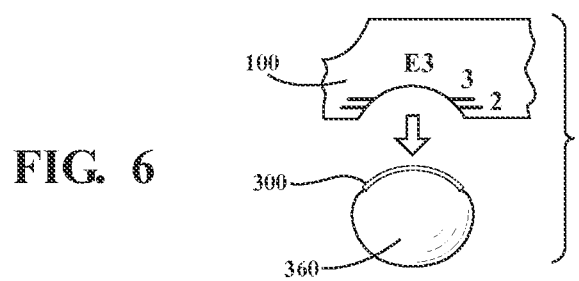
FIG. 6 is a front view of using the nail gauge to measure a fingernail.
Figure 7:
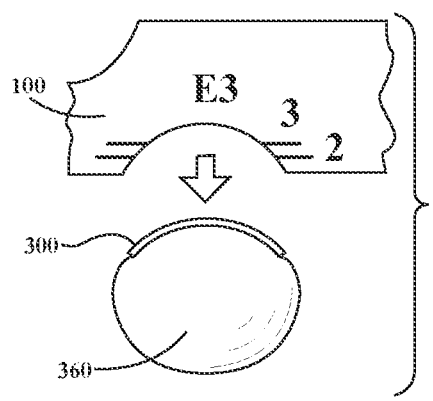
FIG. 7 is a close-up front view of using the nail gauge to measure a fingernail.
Figure 8:
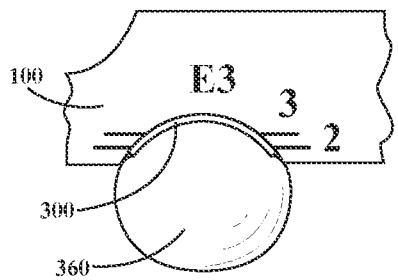
FIG. 8 is a close-up front view of using the nail gauge to measure the fingernail with E3 opening matching the shape of the fingernail.

With added reference to FIGS. 4-6, when using the nail gauge 100 to measure the natural nail 300 on the finger 360, the nail gauge is placed over the nail and is perpendicular to the finger. Moving the nail gauge 100 down onto the natural nail 300 lets one of the arch-shaped openings contact with the natural nail to check whether or not the arch-shaped opening matches with the shape of the natural nail. With further reference to FIGS. 7-10, when the nail gauge 100 is moved down onto the natural nail to check the match between the natural nail 300 and one of the arch-shaped openings such as E3, there are three possible outcomes. A perfect-match is found which leaves no, or minimum, gap 200 (FIG. 8) between the arch-shaped opening and the nail, which means the natural nail 300 is shaped exactly the same as the curved shape corresponding to E3. In addition, the arc length of the natural nail is determined by the arc length marker "2" (FIG. 8) since the natural nail stops at the arc length marker "2". As a result, the measurement result of natural nail 300 is designated as "2E3", with "2" representing the nail arc length information and "E3" referring to the nail arch shape.

Figure 9:
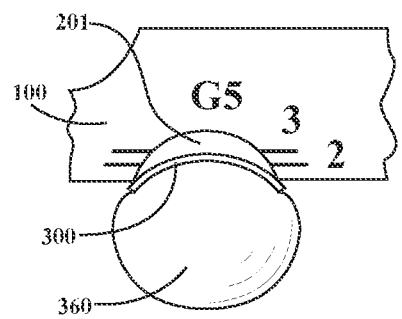
FIG. 9 is a close-up front view of using the nail gauge to measure the fingernail with G5 opening not matching the shape of the fingernail.
Figure 10:
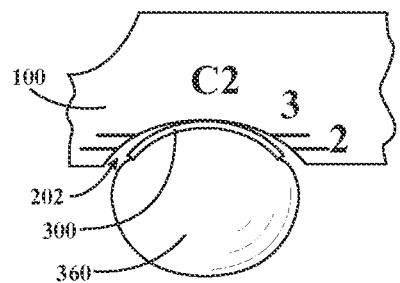
FIG. 10 is a close-up front view of using the nail gauge to measure the fingernail with C2 opening not matching the shape of the fingernail.

With special attention to FIG. 9, if arch-shaped opening G5 is used to measure the natural nail 300, a top gap 201 exists between the two because the G5 opening has a more acute arched shape, which means natural nail 300 does not take the shape of G5. With special attention to FIG. 10, if an arch-shaped opening is too flat to match the nail, a side gap 202 is formed on both sides of the natural nail. By trying different arch-shaped openings of the nail gauge 100 when placed on the natural nail 300, a best match can be found which forms the smallest (nearest to zero) gap. Then by using the arc length markers next to the best fitting arch-shaped opening, the arc length of the natural nail can be determined. As a result, every measured nail can be assigned a special measurement code, which consists of the nail arc length information and the best-matching arch-shaped opening, such as "2A3", "3A5", "2C3", etc. These codes are used to manufacture custom-fit artificial nails as disclosed in United States Patent Application No. 2014/0183769-A1, titled "A System and Method for Manufacturing Custom-Fit Three-Dimensional Artificial Nails" to Li et al., incorporated herein by reference.

Preferred embodiments of present invention are described by way of illustration rather than limitation. Variations of these preferred embodiments may become apparent to those of ordinary skill in the art upon reading the foregoing description. Such variations that do not depart from the gist of the invention are intended to be within the scope and of the invention. The inventors expect skilled artisans to utilize such variations as appropriate, and the inventors intend for the invention to be practiced otherwise than as specifically described herein.

What is claimed is:

1. A nail gauge tool for measuring a natural nail's shape and size along the width of the fingernail, the nail gauge comprising:
    a measurement member having a length, width and thickness wherein along the length of the measurement member are a plurality of arch-shaped openings of different configurations of shape and width, and a plurality of arc length identifiers in proximity to at least one of said arch-shaped openings wherein the arch-shaped openings match with different arch shapes of a natural fingernail and the arc length identifiers match with different arc lengths of the natural fingernail measured along the width of the natural fingernail, whereby both the arch shape and the arc length of the natural fingernail are measured in at least one of said arch-shaped openings.

2. The nail gauge tool of claim 1 wherein the measurement member is composed of at least one of wood, metal and plastic materials.

3. The nail gauge tool of claim 1 wherein each of said plurality of arch-shaped openings are adapted to measure both the arch shape and arc length of a natural nail.

4. The nail gauge tool of claim 1 wherein the measurement member further comprises identifier markings in proximity to each of said plurality of arch-shaped openings.

5. The nail gauge tool of claim 4 wherein the identifier markings correspond to a selection of shapes and sizes of artificial nails.

6. The nail gauge tool of claim 1 wherein said arch-shaped opening are formed by a curved edge with a specific predefined shape.

7. The nail gauge tool of claim 1 wherein said arc length marker is used to designate a certain arc length along the curved edge of the arch-shaped opening.

* * * * *